United States Patent [19]

Bemish et al.

[11] Patent Number: 5,237,098

[45] Date of Patent: Aug. 17, 1993

[54] PRODUCTION OF CITRIC ACID AND TRISODIUM CITRATE FROM MOLASSES

[75] Inventors: Timothy A. Bemish, Bremen; John P. Chiang, Elkhart; Bhalchandra H. Patwardhan, Elkhart; David J. Solow, Elkhart, all of Ind.

[73] Assignee: Miles, Inc., Elkart, Ind.

[21] Appl. No.: 958,950

[22] Filed: Oct. 9, 1992

[51] Int. Cl.$^5$ ............................................. C07C 59/265
[52] U.S. Cl. .................................................. 562/584
[58] Field of Search ................................. 562/584, 580

[56] References Cited

U.S. PATENT DOCUMENTS

| | | | |
|---|---|---|---|
| 3,944,606 | 3/1976 | Rieger et al. | 260/535 |
| 4,275,234 | 6/1981 | Baniel et al. | 562/584 |
| 4,308,398 | 12/1981 | Borchert | 562/584 |
| 4,444,881 | 4/1984 | Urbas | 562/584 X |
| 4,720,579 | 1/1988 | Kulprathipanja | 562/580 |
| 4,855,494 | 8/1989 | Margureanu et al. | 562/580 |
| 4,994,609 | 2/1991 | Baniel et al. | 562/584 X |
| 4,997,489 | 3/1991 | Rabinowitz | 562/584 X |
| 5,032,686 | 7/1991 | Duflot et al. | 562/580 |
| 5,041,645 | 8/1991 | Alon et al. | 562/584 |

*Primary Examiner*—Arthur C. Prescott
*Attorney, Agent, or Firm*—L. E. Davidson

[57] ABSTRACT

A water-immiscible organic extractant system can economically be used to recover citric acid from molasses fermenter beer containing a high salt content by using a process combination of passing the aqueous raffinate from the citric acid extraction step through a basic anion-exchange resin to adsorb residual citric acid and release citrate anions from previously formed salt cation-citrate compounds. Trisodium citrate is then eluted from the resin by passing aqueous sodium hydroxide therethrough.

7 Claims, No Drawings

PRODUCTION OF CITRIC ACID AND TRISODIUM CITRATE FROM MOLASSES

BACKGROUND AND PRIOR ART

It is known from the disclosure in U.S. Pat. No. 4,720,579, for example, that an aqueous citric acid-containing solution can be produced by the fermentation of molasses by an *Aspergillus niger* microorganism strain. It is further known from the disclosure in U.S. Pat. No. 4,275,234 that citric acid can be recovered from aqueous solutions thereof, such as fermenter beer, by a liquid-liquid extraction process using an amine-organic solvent mixture as an organic extractant followed by back-extraction with hot water. A variation of this process is disclosed in U.S. Pat. No. 3,944,606 wherein the back-extraction is accomplished with an alkaline solution to recover the product as a citrate salt instead of citric acid. This organic extractant, however, is unable to remove most of the citric acid from the molasses fermenter beer because of the high salt content, such as potassium salts, of such beer. The salts compete with the amine to complex or react with the citric acid. It is uneconomical to attempt to remove the high salt content of the fermenter beer by use of decationizing materials prior to contact with the organic extractant. For the above reasons, it has been considered impractical to use the above amine-organic solvent mixture extraction process to recover citric acid from molasses fermenter beer. Various adsorbent materials have been disclosed in the prior art to recover citric acid from fermenter beer. U.S. Pat. No. 4,720,579 discloses the use of a neutral cross-linked polystyrene polymer or a nonionic, polyacrylic ester polymer to adsorb citric acid and separate it from various impurities. The citric acid is then desorbed in a purified form. U.S. Pat. No. 4,855,494 discloses the use of nonionic adsorbent resins, cation exchange resins and anion exchange resins to selectively adsorb or otherwise remove various impurities from citric acid solutions. U.S. Pat. No. 5,032,686 discloses the use of a cation exchange resin in the hydrogen form to adsorb citric acid and separate it from various impurities. The purified citric acid is then desorbed in an eluate. None of this prior art, either alone or in any combination, discloses or suggests any processes for recovering residual citric acid in the form of trisodium citrate from the raffinate produced when an amine-organic solvent organic extractant is used to recover citric acid from a molasses fermenter beer. Such process variation enables such overall extraction process to be economically practical for recovering citric acid from molasses fermenter beer.

SUMMARY OF THE INVENTION

In accordance with the present invention, a process for the production of citric acid and trisodium citrate from molasses is provided which comprises the steps of (1) fermenting molasses with an appropriate microorganism to produce a biomass and an aqueous fermenter beer containing citric acid and salts from the molasses, (2) separating the biomass from the fermenter beer, (3) contacting the fermenter beer with a water-immiscible organic extractant which comprises a solution of at least one secondary or tertiary amine in which the aggregate number of carbon atoms is at least 20 and a water-immiscible organic solvent selected from the class consisting of aliphatic hydrocarbons, aromatic hydrocarbons, petroleum fractions, hydrocarbons carrying nitro or halo substituents, alcohols and mixtures thereof to form an organic extract containing citric acid and an aqueous raffinate containing some of the citric acid and all of the salts, (4) subjecting the organic extract to a stripping operation with an aqueous liquid at a temperature higher than the temperature at which the extraction is performed for back-extracting the citric acid from the organic extract into the aqueous liquid and leaving the amine in the organic phase, (5) separating the citric acid-containing aqueous back-extract from the stripped organic extractant to form a first citric acid-containing product, (6) passing the aqueous raffinate from step (3) through at least one basic anion-exchange resin column to adsorb the citric acid and separate it from the salts, and (7) eluting the adsorbed citric acid from the basic anion-exchange column by passing an aqueous solution of sodium hydroxide therethrough to form an effluent aqueous solution which is a second trisodium citrate-containing product.

DESCRIPTION OF THE INVENTION

The conditions for the fermentation of molasses and subsequent treatment to produce a fermenter beer containing citric acid are well-known in the art and need not be repeated here.

The water-immiscible organic extractant useful in the present invention comprises a solution of at least one secondary or tertiary amine in which the aggregate number of carbon atoms is at least 20 and a water-immiscible organic solvent selected from the class consisting of aliphatic hydrocarbons, aromatic hydrocarbons, petroleum fractions, hydrocarbons carrying nitro or halo substituents, alcohols and mixtures thereof. In particular, the preferred amine is trilaurylamine and the preferred organic solvent is a petroleum fraction. It is also preferred that the extractant contain a minor amount of octanol.

After the amine-containing organic extractant removes the citric acid from the fermenter beer, it is separated from the aqueous raffinate, and the citric acid is recovered from the organic extract by back-extraction with an aqueous liquid at a temperature higher than the temperature at which the extraction is performed. Preferably, the back-extraction is conducted at a temperature at least 20 degrees C. above the initial extraction temperature. The extraction operation will as a rule be performed as a multi-stage continuous counter-current process, and the stripped organic extractant will be continuously recycled to the extraction stage. In view of the large amount of color bodies present in the molasses fermenter beer which are also extracted by the organic extractant, it is preferred to contact the stripped organic extractant with an aqueous sodium hydroxide solution to remove color bodies from such extractant before it is recycled to the extraction stage. The back-extracted aqueous citric acid solution can be used as-is as an industrial grade liquid citric acid or it can be subjected to evaporation crystallization, for example, to form a pure food grade citric acid.

The aqueous raffinate from the initial extraction stage is passed through a basic anion-exchange resin column to selectively adsorb the citric acid contained therein and separate it from the salt impurities. Any potassium citrate, for example, contained within the raffinate which resulted from reactions between the potassium salt impurities in the molasses and the citric acid will be converted to other water-soluble potassium compounds depending upon the particular composition of the anion-exchange resin used. These compounds will pass out of the resin column. The thus-freed citrate anions will be retained by the resin for subsequent elution. Preferably, the basic anion-exchange material is in two columns. The first column will contain a weakly-basic anion-exchange material, such as Reillex 425 or Duolite A-561, while the second column will contain a strongly-basic anion-exchange material, such as Amberlite IRA-402 or Ionac A-651. This two-stage anion-exchange procedure maximizes the useful capacity of the anion exchange materials. These anion-exchange materials are well-known and generally consist of a porous resin structure, such as acrylic or styrene cross-linked with divinylbenzene, containing amine functional groups. The weakly-basic anion-exchange materials generally employ primary, secondary, or tertiary amines, such as pyridine or mixtures thereof while the strongly-basic anion-exchange materials contain quaternary ammonium functional groups. The strongly-basic material will also selectively adsorb any color bodies from the raffinate. The adsorbed citric acid along with any citrate anions obtained from the potassium citrate, for example, in the raffinate are eluted from the resins by passing an aqueous solution of sodium hydroxide therethrough to form an effluent solution of trisodium citrate. Preferably, this effluent solution is contacted with carbon to remove any residual color and is subjected to evaporation crystallization to form a pure trisodium citrate product. The strongly-basic resin material can be subsequently treated with an alkaline brine solution to remove any color bodies adsorbed thereon.

This overall process enables the total recovery of citric acid plus trisodium citrate to economically justify the use of the amine-solvent extraction process to treat molasses fermenter beer.

The invention is described in further detail in the following examples.

EXAMPLE 1

Clarified crude fermenter beer containing 15 weight percent citric acid was obtained by culturing a strain of *Aspergillus niger* on molasses and filtering off the resulting biomass. This aqueous fermenter beer was then contacted at 22 degrees C. with an organic extractant consisting of a mixture of 34 percent trilaurylamine, 5 percent octanol and 61 percent petroleum fraction (Shellsol-80), such percents being on a weight/weight basis, in a four-stage counter current "Normag" mixer/settler apparatus. There was an extractant:beer volume ratio of 2.2:1, and 54 weight percent of the citric acid was transferred to the organic phase which contained 3.5 percent citric acid on a weight/volume basis. The citric acid-containing organic phase was then separated from the aqueous raffinate and back-extracted in the same apparatus with water at 90 degrees C. in an extractant:water volume ratio of 7:1. This produced an aqueous product containing 20.5 percent citric acid on a weight/weight basis and a stripped organic phase containing 0.2 percent citric acid on a weight/volume basis. A 300 ml. portion of the raffinate obtained above containing 6 percent citric acid on a weight/weight basis and having an optical density of 3.3, measured at 455 nm, was then passed through two basic anion-exchange resin columns in series. The first column contained 100 ml. of weakly-basic Reillex 425 resin and the second column contained 100 ml. of strongly-basic Amberlite IRA-402 resin. The adsorbed citric acid and any citrate anions from salt impurities in the raffinate were eluted from both of the columns by passing therethrough 200 ml. of 15 percent, weight/weight basis, aqueous sodium hydroxide solution to give 130 ml. of product containing 12.2 percent trisodium citrate on a weight/weight basis, and having an optical density of 0.3, measured at 455 nm. This product was then contacted with granular carbon to remove any residual color and subjected to evaporation crystallization to form a pure trisodium citrate product.

EXAMPLE 2

The stripped organic phase that was separated from the citric acid-containing back-extract of Example 1 was contacted with a 4 percent aqueous sodium hydroxide solution, on a weight/weight basis. About 100 percent, on a visual basis, of the color present in such organic phase was transferred to the aqueous alkaline phase. The so-treated organic phase was then separated from the aqueous phase and reused for extracting citric acid from molasses fermenter beer with identical efficiency as fresh organic extractant.

What is claimed is:

1. A process for the production of citric acid and trisodium citrate from molasses which comprises the steps of (1) fermenting molasses with an appropriate microorganism to produce a biomass and an aqueous fermenter beer containing citric acid and salts from the molasses, (2) separating the biomass from the fermenter beer, (3) contacting the fermenter beer with a water-immiscible organic extractant which comprises a solution of at least one secondary or tertiary amine in which the aggregate number of carbon atoms is at least 20 and a water-immiscible organic solvent selected from the class consisting of aliphatic hydrocarbons, aromatic hydrocarbons, petroleum fractions, hydrocarbons carrying nitro or halo substituents, alcohols and mixtures thereof to form an organic extract and an aqueous raffinate containing some of the citric acid and all of the salts, (4) subjecting the organic extract to a stripping operation with an aqueous liquid at a temperature higher than the temperature at which the extraction is performed for back-extracting the citric acid from the organic extract into the aqueous liquid and leaving substantially all the amine in the organic phase, (5) separating the citric acid-containing aqueous back-extract from the stripped organic extractant to form a first citric acid-containing product, (6) passing the aqueous raffinate from step (3) through at least one basic anion-exchange resin column to adsorb the citric acid and separate it from the salts, and (7) eluting the adsorbed citric acid from the basic anion-exchange column by passing an aqueous solution of sodium hydroxide therethrough to form an effluent aqueous solution which is a second trisodium citrate-containing product.

2. A process according to claim 1 wherein the stripped organic extractant from step (5) is contacted with an aqueous sodium hydroxide solution to remove color bodies from such extractant, the decolorized extractant is separated from the aqueous solution and is recycled for use as an organic extractant to remove citric acid from the fermenter beer.

3. A process according to claim 1 wherein the organic extractant consists of a mixture of 34 percent trilaurylamine, 5 percent octanol and 61 percent petroleum fraction, such percents being on a weight/weight basis.

4. A process according to claim 1 wherein in step (6) the aqueous raffinate is passed in series through a weakly-basic anion-exchange resin column and a strongly-basic anion-exchange resin column.

5. A process according to claim 4 wherein the weakly-basic anion-exchange resin column contains Reillex 425 and strongly-basic anion-exchange resin column contains Amberlite IRA-402.

6. A process according to claim 1 wherein the aqueous trisodium citrate solution from step (7) is contacted with carbon to remove residual color and is then subjected to evaporation crystallization to form a pure trisodium citrate product.

7. A process according to claim 4 wherein the strongly-basic anion-exchange resin column is subsequently treated with an alkaline brine solution to remove color bodies adsorbed thereon.

* * * * *